(12) United States Patent
Allmendinger et al.

(10) Patent No.: US 8,259,898 B2
(45) Date of Patent: Sep. 4, 2012

(54) METHOD FOR PREDICTING SPECIFIC CYCLE PHASES OF A BEATING HEART IN A PATIENT WITHIN THE SCOPE OF A CT EXAMINATION AND CT SYSTEM

(75) Inventors: Thomas Allmendinger, Forcheim (DE); Steffen Kappler, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/911,335

(22) Filed: Oct. 25, 2010

(65) Prior Publication Data
US 2011/0096893 A1 Apr. 28, 2011

(30) Foreign Application Priority Data
Oct. 27, 2009 (DE) .................. 10 2009 050 769

(51) Int. Cl.
*A61B 6/00* (2006.01)
(52) U.S. Cl. ................................. 378/8; 378/4
(58) Field of Classification Search ........................ 378/8
See application file for complete search history.

(56) References Cited

U.S. PATENT DOCUMENTS

| | | | | |
|---|---|---|---|---|
| 5,271,055 A * | 12/1993 | Hsieh et al. | ...................... | 378/95 |
| 6,434,215 B1 * | 8/2002 | Cesmeli | ............................ | 378/8 |
| 6,510,337 B1 * | 1/2003 | Heuscher et al. | ............. | 600/428 |
| 6,708,052 B1 * | 3/2004 | Mao et al. | ...................... | 600/407 |
| 6,937,696 B1 * | 8/2005 | Mostafavi | ............................. | 378/95 |
| 7,295,693 B2 * | 11/2007 | Kaufman et al. | ............. | 382/131 |
| 7,454,043 B2 * | 11/2008 | Eck et al. | ....................... | 382/128 |
| 7,505,552 B2 * | 3/2009 | Bruder | ............................... | 378/8 |
| 7,630,472 B2 * | 12/2009 | Tsuyuki et al. | .................. | 378/8 |
| 7,818,046 B2 | 10/2010 | Bruder et al. | | |
| 8,073,213 B2 * | 12/2011 | Vaillant et al. | ................. | 382/128 |
| 2005/0089133 A1 * | 4/2005 | Tsuyuki | ............................ | 378/8 |
| 2006/0120581 A1 * | 6/2006 | Eck et al. | ....................... | 382/128 |
| 2006/0280283 A1 | 12/2006 | Hsieh et al. | | |
| 2007/0032735 A1 | 2/2007 | Bruder et al. | | |
| 2007/0140411 A1 * | 6/2007 | Manzke et al. | ................... | 378/8 |
| 2008/0165919 A1 * | 7/2008 | Bruder et al. | ...................... | 378/8 |
| 2009/0060120 A1 * | 3/2009 | Mukumoto et al. | .............. | 378/8 |

FOREIGN PATENT DOCUMENTS

DE 102005036963 B3 2/2007
DE 102006027045 A1 3/2007

OTHER PUBLICATIONS

German priority document DE 10 2009 050 769.8, filed Oct. 27, 2009, not yet published.

* cited by examiner

*Primary Examiner* — Alexander H Taningco
(74) *Attorney, Agent, or Firm* — Harness, Dickey & Pierce, P.L.C.

(57) ABSTRACT

A method and a CT system are disclosed for predicting specific cardiac cycle phases within the scope of a CT examination, wherein signal profiles of the heart are continuously recorded during the examination over a plurality of cardiac cycles, wherein times of successive cycle positions with the same characteristics are determined with the aid of the signal profiles and the successive cycle lengths of the cardiac cycles are determined with the aid of the determined times, wherein typical patterns in successive cycle lengths over a first number of past and successive cardiac cycles are sought after and a current or future cycle length is determined by recording cycle patterns in a second, smaller number of cycle lengths including their typical successive cycle length within the first number of current past cycle lengths, and predicting, using probabilistic methods, the cycle length that follows the last determined cycle pattern on the basis of the cycle patterns currently determined during the CT examination.

14 Claims, 6 Drawing Sheets

ID FOR PREDICTING SPECIFIC
METHOD FOR PREDICTING SPECIFIC CYCLE PHASES OF A BEATING HEART IN A PATIENT WITHIN THE SCOPE OF A CT EXAMINATION AND CT SYSTEM

PRIORITY STATEMENT

The present application hereby claims priority under 35 U.S.C. §119 on German patent application number DE 10 2009 050 769.8 filed Oct. 27, 2009, the entire contents of which are hereby incorporated herein by reference.

FIELD

At least one embodiment of the invention generally relates to a method for predicting specific cycle phases of a beating heart in a patient within the scope of a CT examination, wherein typical patterns are identified in previously recorded signal profiles of the heart, which patterns are respectively followed by a characteristic cardiac cycle, and the lengths of such cardiac cycles are predicted. Furthermore, at least one embodiment of the invention relates to a CT system for carrying out this method.

BACKGROUND

The selected cardiac phase is a decisive criterion for good image quality in cardiac imaging using CT. Therefore, reliably predicting the cardiac cycle length is the central criterion for all prospective cardiac CT modes (sequence, high-pitch spiral). Without high-quality predictions, prospectively-triggered scans cannot be performed reliably and the desired image quality is not obtained.

According to the current prior art, a relatively simple mechanism is used in practice for predicting the time of the next R wave. This is usually the median value from the length of the last three cardiac cycles, with, additionally, an interval being determined within which the next R wave occurs. In the process, the interval is calculated with the aid of the variance of the heart rate. During the CT examination, the dose power of the X-ray tube can be controlled using the calculated interval such that there is maximum dose power available during the respective rest phase used for the reconstruction, but only little or no radiation dose is applied in cycle phases that are less relevant for imaging. As a result, the data in the desired cardiac phase is first of all available in the subsequent reconstruction, but the applied radiation dose overall is kept as low as possible. In most cases this procedure is sufficient and leads to good results.

However, there are patients that have arrhythmic cardiac cycles, for example as a result of ventricular extrasystoles, and so the above-described averaging over a number of cardiac cycles does not lead to a reliable prediction of cycle lengths. However, such arrhythmic cardiac cycles have typical patterns over a number of cycles and these can be identified by correspondingly longer observation, making predictions possible. Accordingly, it is also well-known to identify such patterns using long-term EKGs, evaluate them statistically and then make corresponding predictions.

However, the problem with such predictions on the basis of long-term EKGs lies in the fact that at the time of recording a long-term EKG there are, in principle, different living conditions than during the CT examination, and as a result, physical and mental states, which occur during the CT examination and influence the cardiac rhythm, do not occur in advance and therefore cannot be taken into account. Furthermore, cardiac CT examinations are generally performed under the administration of contrast agents that likewise heavily burden the circulatory system. This situation too can only be included in the measurements in advance with great difficulty.

SUMMARY

In at least one embodiment of the invention, a method and CT system are disclosed that obtain prediction data from measurements during the actual examination and, however, at the same time also reliably predict arrhythmic cardiac cycles.

Advantageous developments of the invention are the subject matter of the dependent claims.

The inventors have recognized that it is possible to predict arrhythmic cardiac cycles on the basis of a relatively small number of current measurements, usually within the limits of 5 to 20 preceding cardiac cycles, and with high reliability on the basis of a probability density estimate. For this purpose, a shortened cycle pattern, recorded over a small number of cardiac cycles, in the form of state vectors can be transferred into a state space, with each state vector being assigned the value of the subsequent cycle length. By forming a weighted average over the subsequently measured cycle lengths, it is possible to predict the value of a future cycle to a good approximation if the utilized weightings are inversely proportional to the distance between the state vectors recorded for the cycle length and the currently considered state vector for which the prediction should be made. In the process, an inverse proportionality is particularly expedient, which places the distances to the power of the dimension of the state vectors into the denominator. In general terms, this means that there is a probabilistic prediction of the cycle length that follows the last determined cycle pattern on the basis of the current cycle patterns established during the CT examination.

The upshot of this is that the system also reacts to cycle patterns and makes very good predictions of cycle lengths that occur in relatively long intervals or are irregular, without necessitating a long examination and evaluation of long-term EKGs. Moreover, the method described here is advantageous in that it also reacts to short-term changes in the cardiac cycle that did not occur before the CT examination. However, if there is a regular cardiac rhythm, the prediction results correspond to simple forming of a median, as is known from the prior art.

In accordance with this information, in at least one embodiment the inventors propose a method for predicting specific cycle phases of a beating heart in a patient within the scope of a CT examination, wherein signal profiles of the heart are continuously recorded during the examination over a multiplicity of cardiac cycles, and the following method steps are carried out:

determining times of successive cycle positions with the same characteristics with the aid of the signal profiles and the characteristic signal profiles contained therein, determining successive cycle lengths of the cardiac cycles with the aid of the determined times, seeking, progressively concurrently with the present time, typical patterns in successive cycle lengths over a predetermined first number of past and successive cardiac cycles, determining a current or future cycle length by:

recording cycle patterns in a second, smaller number of cycle lengths including their typical subsequent cycle length within the first number of current past cycle lengths, and predicting, using probabilistic means, the cycle length that follows the last determined cycle pattern on the basis of the cycle patterns currently determined during the CT examination.

In the process of determining the cycle length to be predicted, a weighting should be used that is inversely proportional, more particularly inversely proportional to the power of the second number. In respect of this weighting, reference is also made to the fact that the effect thereof can firstly be influenced with the aid of a constant factor. Secondly, program-technical precautions should also be made to prevent a method or program termination when identity with preceding measurement values would lead to infinite weighting due to a division by the distance "zero". By way of example, a small constant factor can be added to the calculated distance in the denominator, or a predetermined weighting can be used if the distance assumes a value of close to zero or zero.

Once the cycle length has been predicted, the position in time of a certain cycle region can be predicted using the predicted cycle length. By way of example, it is conventional in this case to specify a rest phase in the determined percentage range of the cycle length.

At least one embodiment of the aforementioned method can principally be used within the scope of a CT scan to adjust a dose power of at least one X-ray tube operational for the scan using the predicted position in time of the cycle region.

Furthermore, if image reconstruction takes place within the scope of the CT examination, during which reconstruction only detector data from prescribed cardiac cycle phases should be used, or this data should be particularly heavily weighted, this method of at least one embodiment can also be used to determine the prescribed cardiac cycle phases of each cycle individually on the basis of the predicted cycle length.

A more specific special embodiment of the method can comprise the following method steps:

measuring the cycle lengths within an overall interval with a specific overall number N of successive cardiac cycles before the current cycle, forming subintervals, which overlap where necessary, with few L successive cycles within this overall interval, and determining a state vector in an L-dimensional space and the associated cycle length of the subsequent cardiac cycle in each subinterval, with L corresponding to the number of successive cycles in each subinterval, determining the cycle length of the current cardiac cycle by calculating a weighted average from the assigned cycle lengths, wherein the weighting is inversely proportional, more particularly inversely proportional to the power of the dimension of the L-dimensional space of the state vectors, to the Euclidean distance between the considered state vector with the subsequent cycle length to be predicted and the other state vectors with known subsequent cycle lengths in the L-dimensional space.

In the process, the cycle length $\hat{C}(\vec{Z})$ to be predicted is calculated by:

$$\hat{C}(\vec{Z}) = \frac{\sum_{j=L+1}^{N} w(j) \cdot C(j)}{\sum_{i=L+1}^{N} w(j)}$$

wherein the following holds true for the weightings w(j):

$$w(j) = \frac{1}{V_0 + K_L |\vec{Z} - \vec{Z}(j)|^L},$$

where:
C(j) are the cycle lengths,
$K_L$ is a constant factor,
$\vec{Z}(j)$ are the state vectors,
$\vec{Z}$ is the state vector, for which the subsequent cycle length should be predicted.

Whereas cycle lengths were considered directly in terms of their absolute values in the aforementioned embodiments, the consideration can also relate to the change in the cycle lengths. The advantage of this is that this affords easier treatments of low-frequency changes in the cycle lengths without upper and lower bounds. Accordingly, the inventors propose a further improved concrete embodiment of the method according to the invention, in which the following method steps are carried out:

measuring the cycle lengths within an overall interval with a specific overall number N of successive cardiac cycles before the current cycle, forming subintervals, which overlap where necessary, with few L successive cycles within this overall interval, and determining a state vector in an L-dimensional space and an associated cycle length change in the subsequent cardiac cycle relative to the average of the cycle lengths in the considered subinterval in each subinterval, with L corresponding to the number of successive cycles in each subinterval, determining the cycle length of the current cardiac cycle and the cardiac cycle to be predicted by:

calculating a weighted average from the assigned cycle length changes, wherein the weighting is inversely proportional, more particularly inversely proportional to the power of the dimension of the L-dimensional space of the state vectors, to the Euclidean distance between the considered state vector with the subsequent cycle length to be predicted and the other state vectors with known subsequent cycle lengths in the L-dimensional space, and adding the weighted average of the cycle length changes to the average of the cycle lengths in the last subinterval.

Herein, the cycle length $\hat{C}(\vec{Z})$ to be predicted can be calculated as follows:

$$\hat{C}(\vec{Z}) = M(\vec{Z}) + \frac{\sum_{j=L+1}^{N} w(j) \cdot C^*(j)}{\sum_{i=L+1}^{N} w(j)}$$

wherein the following holds true for the weightings w(j):

$$w(j) = \frac{1}{V_0 + K_L |\vec{Z} - \vec{Z}(j)|^L},$$

where:
$K_L$ is a constant factor,
$\vec{Z}(j)$ are the state vectors, $\vec{Z}$ is the state vector, for which the subsequent cycle length should be predicted, M ($\vec{Z}$) is the average over the components of the state vector $\vec{Z}$, M ($\vec{Z}$(j)) is the average over the components of the state vector $\vec{Z}$(j), C*(j)=C(j)−M($\vec{Z}$(j)) is the cycle length change calculated from the difference between the subsequent cycle length and the average of the components of the state vector $\vec{Z}$(j).

In principle, the aforementioned method can particularly preferably be applied to signal profiles in which the cardiac signals are electrical potentials of the heart, that is to say in conjunction with electrocardiograms. However, the method is not restricted to this, pressure changes in or on the arterial circulatory system can also be used to record the cardiac signal profiles. Moreover, ultrasound measurements and results from online imaging can also be used.

In addition to the method described here, the inventors also propose a CT system in at least one embodiment for carrying out a cardiac scan, having a control and computational unit with a storage medium for storing at least one computer program, which adapts the dosage power depending on the cardiac cycle during operation in order to reduce the dose load on a patient to be scanned, wherein the program for adapting the cardiac-cycle-dependent dose power develops the duration of a current and still ongoing cycle length and/or a cycle region in a still ongoing cardiac cycle such that it carries out at least one embodiment of the method as described above.

BRIEF DESCRIPTION OF THE DRAWINGS

In the following, embodiments of the invention will be described in more detail with the aid of the figures, with only the features required for understanding embodiments of the invention being illustrated. In the process, the following reference signs are used: 1: CT system; 2: X-ray tube; 3: detector; 4: second X-ray tube (optional); 5: second detector (optional); 6: gantry housing; 7: patient; 8: examination couch; 9: system axis; 10: control and computational unit; 11: contrast-agent applicator; 12: EKG line; B: region of high probability for the subsequent cycle to be predicted; F1, F2, F3: cycle lengths in bpm; M: profile of the measured heart rate; $Prg_1$ to $Prg_n$: computer programs; TI-1 to TI-5: subintervals; TE-1 to TE-5: result interval/subsequent interval; TE: sought-after subsequent interval; V: profile of the predicted subsequent cycle.

In detail.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
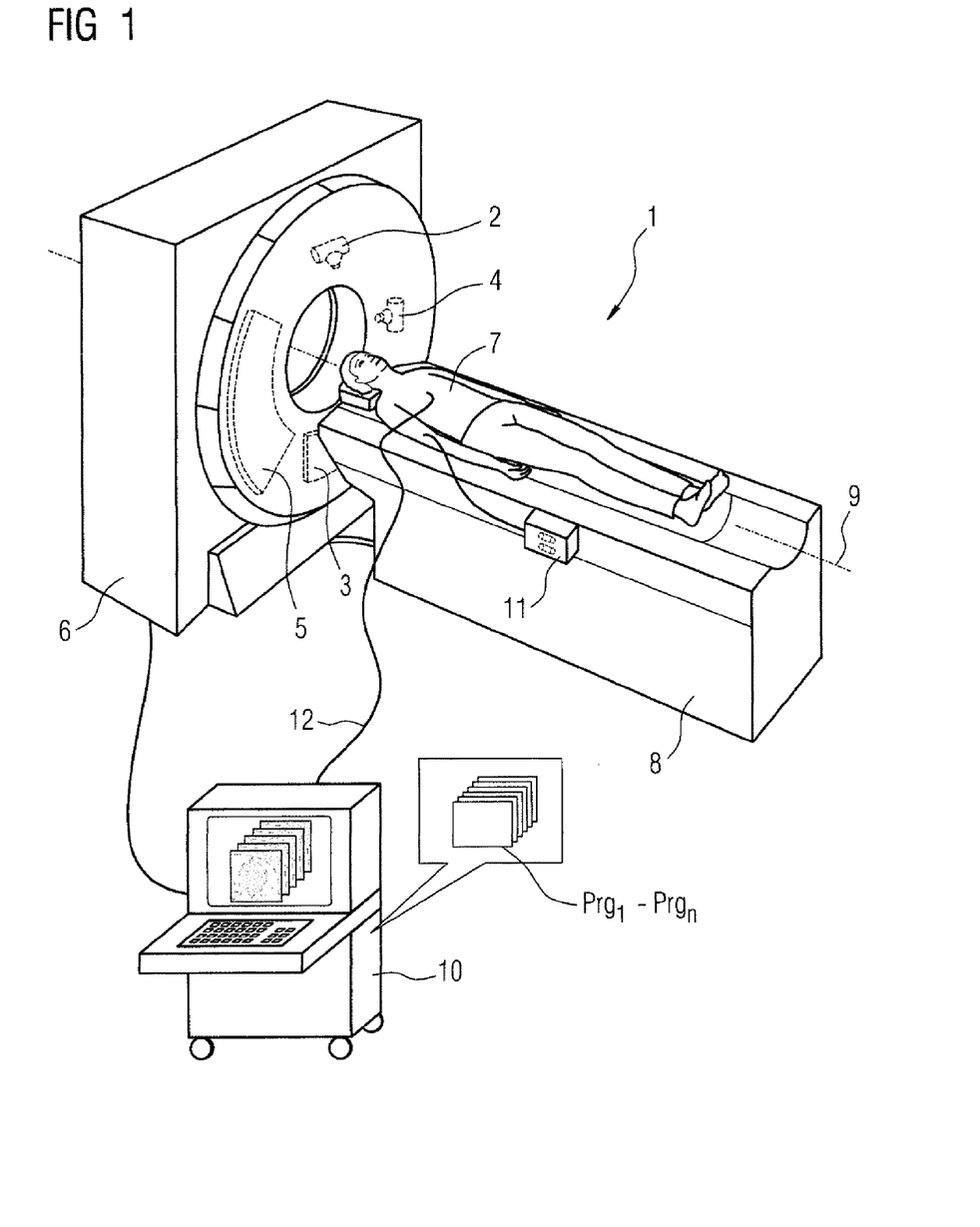
FIG. 1 shows a CT system for carrying out a cardiac CT examination.

FIG. 1 shows, in an example fashion, a schematically illustrated CT system 1 that can be used to carry out the method according to an embodiment of the invention. The CT system 1 has a first tube/detector system with an X-ray tube 2 and an opposing detector 3. This CT system 1 can optionally comprise a second X-ray tube 4 with an opposing detector 5. This can either improve the time resolution or allow scans to be performed simultaneously with different energy spectra. As per the method according to the invention, the dose power of the X-ray tubes can be controlled in both variants.

Both tube/detector systems are located on a gantry (not illustrated here), the latter being arranged in a gantry housing 6 and rotating about a system axis 9 during the scan. It goes without saying that the X-ray tubes and detectors are arranged behind a cover. The patient 7 is located on a displaceable examination couch 8, which is pushed, either continuously or sequentially along the system axis 9, through the scanning field located centrally in the gantry housing 6, with the attenuation of the X-ray radiation emitted by the X-ray tubes being measured by the detectors.

During the measurement, a contrast-agent bolus can be injected into the patient 7 with the aid of a contrast-agent applicator 11, and so it is easier to identify blood vessels. In the case of cardiac recordings, the cardiac activity can additionally be measured with the aid of the EKG line 12 illustrated here or with a pressure pulse sensor, and this allows gated scanning to be carried out.

The CT system is controlled with the aid of a control and computational unit 10, in which computer programs $Prg_1$ to $Prg_n$ are located that can also carry out the above-described method according to the invention. Image data can additionally be output via this control and computational unit 10.

Figure 2:
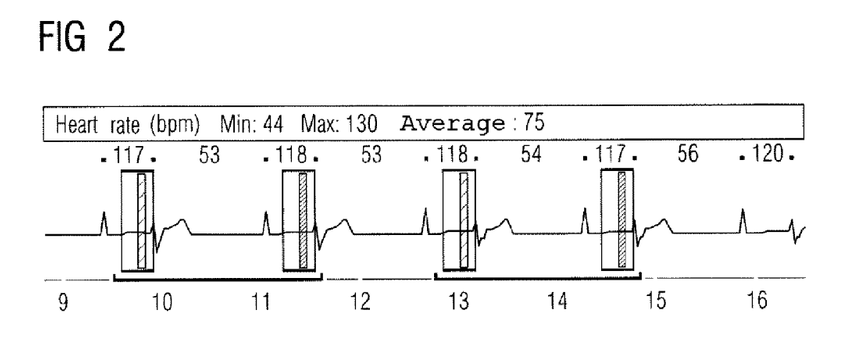
FIG. 2 shows an arrhythmic EKG from a patient with bigeminy.

An example of an arrhythmic property of a heart during a CT scan is shown in FIG. 2. Here there is a typical EKG profile of a patient with bigeminy arrhythmia. Accordingly, alternating short and long successive cardiac cycles can be identified in this case with a heart rate of 117, 53, 118, 53, 118, 54, 117, 56 and 120 bpm. Observed over a relatively long period of time, this EKG resulted in a minimum of 44 bpm and a maximum of 130 bpm, with an average of 75 bpm. If use were made of a method from the prior art, in which the prediction is related to the average value of the heart rate, the predicted rest phases would be incorrect each time and lead to unsatisfactory image results.

In accordance with the idea of an embodiment of the invention sketched out above, the respective next cardiac cycle is determined online during the scan in the illustrated CT system with the aid of corresponding prediction mechanisms on the basis of a certain number of respectively past cardiac cycles and patterns in respect of sequences of cycle lengths contained therein.

The method according to an embodiment of the invention results in a significantly improved prediction on the basis of the principle of estimating the most likely value from an only sparsely-described probability density. The previously detected, n time positions of the R waves R(i) can be used as input data or training data for the algorithm, and the preceding $N=n-1$ cycle lengths $C(i)=R(i)-R(i-1)$, $i=2, \ldots, n$ can be calculated therefrom. Each value of the variable $C(j)$, with $j=L+1, \ldots, N$, can be characterized by a state vector $\vec{Z}(j)=[C(j-L) \ldots C(j-1)]$, which is formed from L>N directly preceding values. Thus, the state vectors $\vec{Z}(j)$ parameterize the last N−L states that the system, i.e. the heart, was in. The associated C(j) specify precisely those values that were true for the system in those states. Furthermore, $\rho(C;\vec{Z})$ describes the only sparsely-known probability density for values of C in the state $\vec{Z}$. Now, a good approximation for the value $\hat{C}$, which is the most likely and can serve as a prediction, should now be found for any state vector $\vec{Z}$. A "sparsely known probability density" is referred to because the utilized data pool is related to a data collection of few items of present past data that have only been recorded during the current scan. That is to say no long-term measurements for determining statistically significant values are used.

Subsequently, $\vec{Z}=\vec{Z}(N+1)$ is selected to predict the unknown value C(N+1) using $\hat{C}$. In the case of fixed $\vec{Z}$, $\hat{C}$ satisfies the condition $\rho(\hat{C};\vec{Z})=\max!$. The assumption is furthermore made that $\rho(C;\vec{Z})$ has an approximately normal distribution for fixed $\vec{Z}$. Then $\hat{C}$ can be calculated by simply averaging the C(j) measured at identical or similar $\vec{Z}$. However, there may only be few or no C(j) present for certain $\vec{Z}$ in the case of a relatively little amount of training data. Advantageously, the following weighted averaging is offered, which uses the C(j) of all states $\vec{Z}(j)$ and prefers those that are closer to the sought-after $\vec{Z}$ in the state-phase space:

$$\hat{C}(\vec{Z}) = \frac{\sum_{j=L+1}^{N} w(j) \cdot C(j)}{\sum_{i=L+1}^{N} w(j)}$$

with the weightings $$w(j) = \frac{1}{V_0 + K_L |\vec{Z} - \vec{Z}(j)|^L},$$

wherein $K_L$ takes the geometry of the L-dimensional space into account and $0 < V_0 \ll 1$ prevents divergence in the case where $\vec{Z} = \vec{Z}(j)$.

Thus, each weighting w(j) corresponds to the reciprocal volume of an L-ball with a radius corresponding to the Euclidean distance d(j) between $\vec{Z}$ and $\vec{Z}(j)$. This empirically selected weighting provides the following advantages:

i) The weightings w(j) represent the information density of the individual values C(j) in the volume of an L-ball with a radius corresponding to the Euclidean distance d(j) between $\vec{Z}$ and $\vec{Z}(j)$. Hence the sum of all weightings provides an absolute measure of the quality of the prediction.

ii) The expected occupancy of the phase space in a training sample generated from real data is calculated using $\Phi(\vec{Z}) = \int \rho(C;\vec{Z})dC$. This means a higher population in regions of higher probability. Hence, these more populated areas contribute more to the prediction using the aforementioned weighting, as a result of which the willingness of the method to take risks is damped. This is a desired effect in medical-technical applications.

iii) Values situated at the same distance contribute equally to calculating $\hat{C}$.

iv) Values very close to $\vec{Z}$ dominate if available. If no values can be found in the vicinity, the algorithm acts similarly to conventional averaging.

Figure 3:
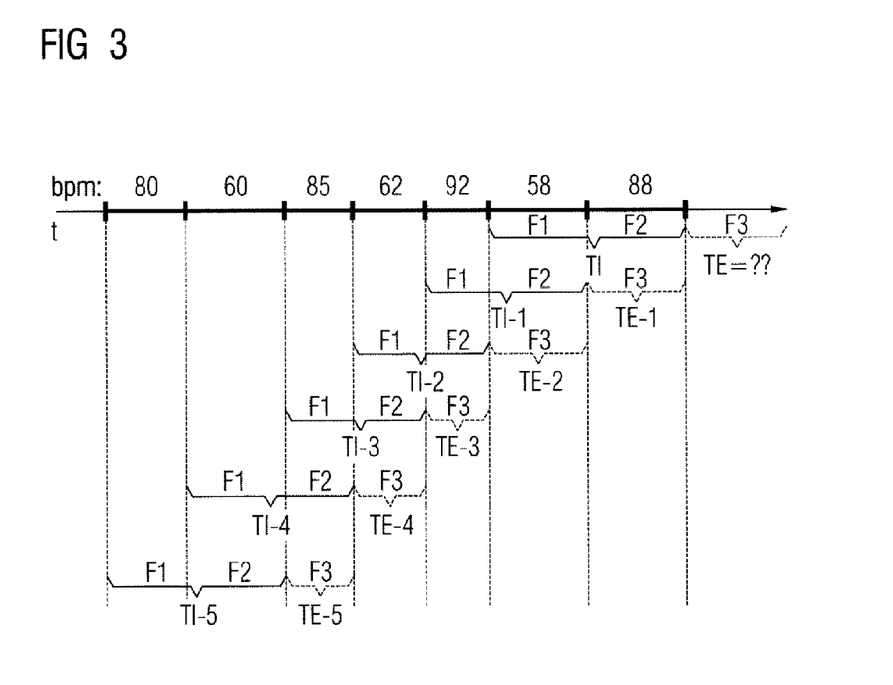
FIG. 3 shows an exemplary sequence of arrhythmic cardiac cycles.
Figure 4:
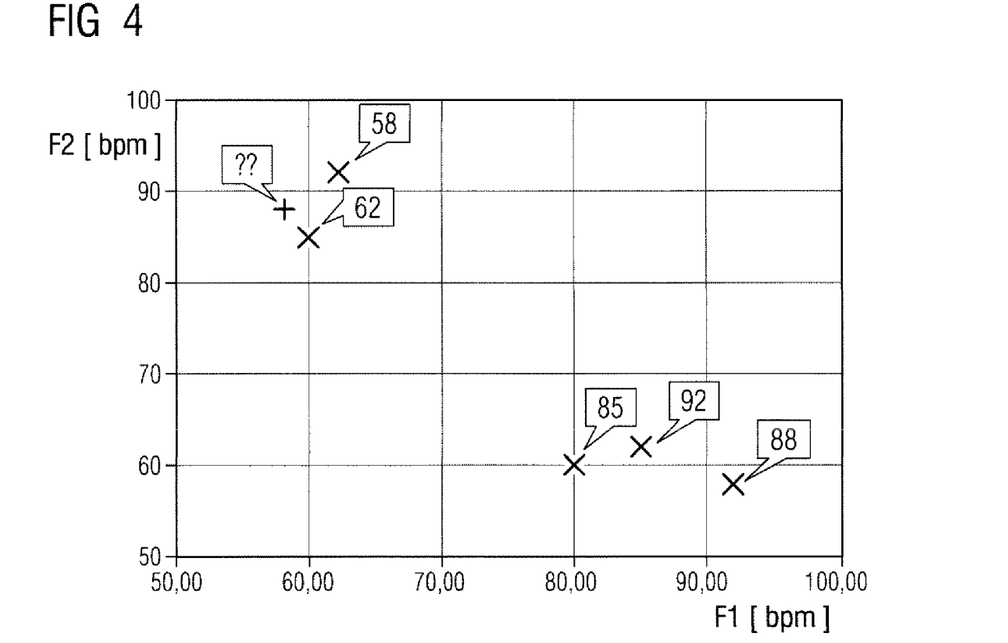
FIG. 4 shows cardiac cycles from FIG. 3, encoded as two-dimensional state vectors and plotted in a two-dimensional state space with the subsequent cycle lengths being specified.

A concrete example of the above-described method based on two-dimensional state vectors is shown in FIGS. 3 and 4. FIG. 3 shows a timeline over time t, on which the cycle lengths of a heart with a bigeminy rhythm are plotted with the corresponding heart rates in beats per minute (bpm). It can be seen that a two-rhythm is generated here, made up from the frequencies F1 and F2 with alternating long and short cardiac cycles, with respectively one subsequent cardiac cycle (=subsequent cycle) at frequency F3. Thus, the overall number of retrospectively considered six cardiac cycles is subdivided into subintervals TI-0 to TI-4, wherein respectively one subsequent result subinterval TE-1 to TE-4 is known and the length of the current result subinterval with the current frequency F3 should be determined.

According to an embodiment of the invention, the value pairs of the respectively two frequencies F1 and F2 can be plotted in the form of state vectors in a two-dimensional state coordinate system, as shown in FIG. 4. The illustration shown here corresponds to the calculation as per claims 6 and 7. In the process, each state vector is assigned the value of the subsequent frequency F3 or the subsequent result interval. If the plotted values are now observed in the coordinate system of FIG. 4, two accumulations of state vectors can be identified, top left and bottom right. The frequencies F3 are specified in the flags at the end points of the vectors. If the current last subinterval TI with the values F1=58 and F2=88 is considered at this point, it can be seen that this subinterval must be very similar to the subintervals TI-4 and TI-2, that is to say it is close to these vectors. Hence a subsequent result interval TE can also be expected in the vicinity of the result intervals TE-4 and TE-2.

Now, it was found empirically that a very good approximation of the result interval to be expected can be obtained by taking into account the average and by inverse proportional weighting of the available result intervals to the power of the dimension of the state vectors, corresponding to the distance between the associated state vectors and the state vector for which the result interval is sought after. In the present example, this means $$TE = \frac{1}{N} \cdot \sum_{j=1}^{4} \frac{1}{V_0 + |\overrightarrow{TI} - \overrightarrow{TI_{-j}}|^2} \cdot TE_{-j},$$

with $$N = \sum_{j=1}^{4} \frac{1}{V_0 + |\overrightarrow{TI} - \overrightarrow{TI_{-j}}|^2}.$$

A further-improved variant of the method according to an embodiment of the invention does not consider the absolute length of the cardiac cycles, but considers their change in each case with respect to the average of the preceding subinterval.

Figure 5:
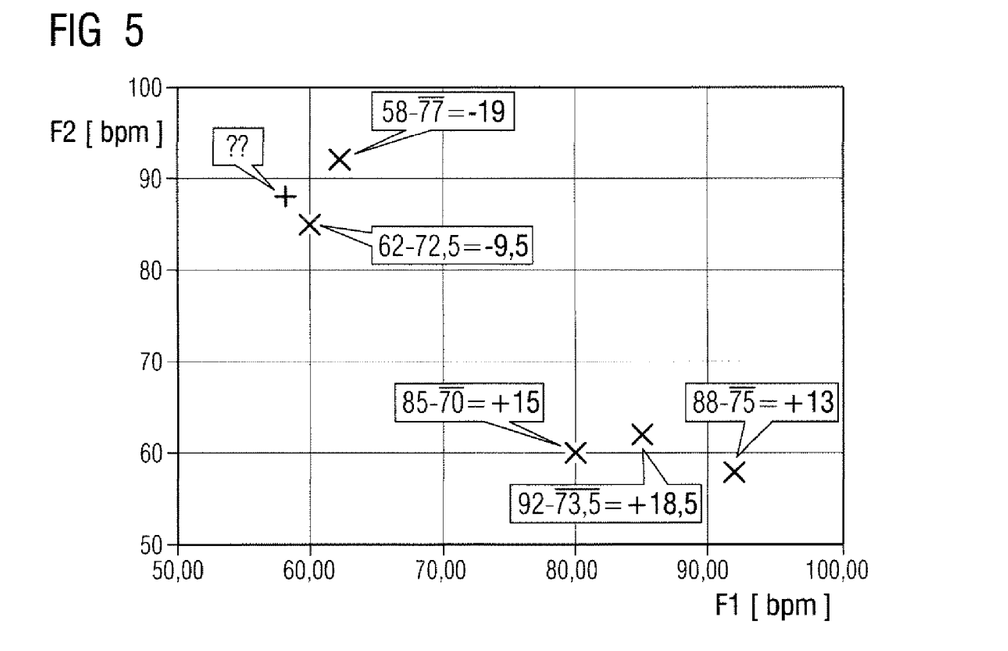
FIG. 5 shows cardiac cycles from FIG. 3, encoded as two-dimensional state vectors and plotted in a two-dimensional state space with the corresponding cycle length change of the subsequent cycle relative to the average of the cycle lengths of the respective state vector being specified.

If the concrete example from FIG. 3 is considered, this results in an illustration of the value pairs of the respective two frequencies F1 and F2, again in the form of state vectors in a two-dimensional state-coordinate system, as shown in FIG. 5. The illustration shown here corresponds to the calculation as per claims 8 and 9. Herein, each state vector (plotted as X) is assigned the value of a cycle length change (=result in the flags) of the subsequent cycle frequency F3 (=first numerical value in the flag) relative to the average (=numerical values with a bar over them) of the cycle lengths from F1 and F2. If the plotted values are now observed in the coordinate system of FIG. 5, two accumulations of state vectors can be identified, top left and bottom right. The cycle length changes of the respective subsequent result intervals, that is to say the respective subsequent cycles TE-1 to TE-5, are specified in the flags at the end points of the vectors. If the current last subinterval TI with the values F1=58 and F2=88 (plotted as +) is considered at this point, it can be seen that this subinterval must be very similar to the subintervals TI-4 and TI-2, that is to say the subsequent cycle length change must also be close to these vectors. Hence, the cycle length change for a subsequent result interval TE can also be expected in the vicinity of the cycle length change of the result intervals TE-4 and TE-2.

It was also found empirically in this case that a very good approximation of the result interval to be expected can be obtained by taking into account the average and by inverse proportional weighting of the cycle length changes of the available result intervals to the power of the dimension of the state vectors, corresponding to the distance between the associated state vectors and the state vector for which the cycle length is sought after.

Mathematically, this can be shown as follows using a further special exemplary embodiment. Herein, the previously detected time positions of the R waves R(i) are used first of all to determine the preceding cycle lengths C(i)=R(i)−R(i−1), i=2, . . . , n. C{1;N}=[C(n−N+1), . . . , C(n)] is used for the further calculation and in this form denotes a vector of length N with a start index 1 and an end index N. Here, the element C{1;1} is the cycle length furthest back in time. The reference C{$N_{Start}$;$N_{Stop}$} now denotes a corresponding subinterval of the overall interval C{1;N}. Here, the conditions $1 \leq N_{Start} \leq N_{Stop} \leq N$ hold true for the start and end indices.

The length of the considered cycle lengths N can become relatively large during the current scan, for example N=9, and so it needs to be ensured that an estimate can also be generated for short intervals with a minimum length $N_{min}$=3. Hence, the following formula holds true for filling missing measurement points, where $N_j \in [N_{min} \ldots N-1]$ have been measured:

$$C^*_N = \lfloor C\{1; N-N_j\}_{avg}, C(N-N_j+1;N) \lceil \quad C_{avg} = \text{mean}(C\{N-N_j+1;N\})$$

The algorithm is constructed as follows: the reference point R, vectors P and V for the position and the value are determined as follows on the basis of the window length $L \in [1 \ldots N-1]$, with a typical length L=3:

$$R = \vec{R} = C\{N-L+1;N\}$$

$$P_{i=1 \ldots N-L} = \vec{P}_{i=1 \ldots N-L} = C\{N-L-i;N-i\}_i$$

$$V_{i=1 \ldots N-L} = C\{N-i+1;N-i+1\} - \text{mean}(C\{N-L-i+1;N-i\})$$

Now the Euclidean distance between the vectors P and the reference R is determined, $D_{i=1 \ldots N-L} = \oplus |\vec{R} - \vec{P}_i|$, and, using this in turn, a volume density:

$$S_{i=1 \ldots N-L} = \frac{1}{V_0 + K \cdot D_i^L},$$

where $V_0$=1 determines a minimum distance in order to avoid a singularity, and K is a constant. The weighting W is now determined from the density S:

$$W_{i=1 \ldots N-L} = \frac{S_{i=1 \ldots N-L}}{\sum_{j=1}^{N-L} S_j}$$

The estimated value for the next cycle length $C_p$ emerges from the formulae above as:

$$C_p = \text{mean}(C\{N-L+1; N\}) + \sum_{j=1}^{N-L} W_j \cdot V_j.$$

The uncertainty σ can be calculated as follows:

$$\sigma = -2 \cdot \log\left(\sum_{j=1}^{N-L} S_i\right),$$

from which, with the aid of the variable Δσ, the upper and lower bounds $C_{min}$ and $C_{max}$ for the most probable interval of the next R wave emerge:

$$\Delta\sigma = \min\left(\max\left(\frac{\sigma}{\Omega_{scale}}\right); \Omega_{min}\right); \Omega_{max}\right) \cdot |\max(W_j \cdot V_j)_j - \min(W_j \cdot V_j)_j|$$

$C_{min}=C_p-\Delta\sigma$ and $C_{max}=C_p+\Delta\sigma$.

Thus, if consideration is given to the training patterns with the subintervals TI−j from FIG. 3, it is not the subsequent cycle length TE−j itself that is used in this case, but the absolute change thereof: (TE−j)−mean(TI−j). Here, in this nomenclature, TI−j is a tuple of a sequence of length L from which an average mean can be formed. The advantage of this is that there is no phase offset between prediction and reality in the case of slow changes in the cycle length, which are for example caused by respiration (see FIGS. 6 and 7). Hence the prediction in FIG. 7 is better than in FIG. 6 despite there being a long-wavelength oscillation.

Accordingly, in concrete terms, a cycle length $\hat{C}(\vec{Z})$ to be predicted can be calculated by:

$$\hat{C}(\vec{Z}) = M(\vec{Z}) + \frac{\sum_{j=L+1}^{N} w(j) \cdot C^*(j)}{\sum_{i=L+1}^{N} w(j)}$$

wherein the following holds true for the weightings w(j):

$$w(j) = \frac{1}{V_0 + K_L |\vec{Z} - \vec{Z}(j)|^L},$$

where:

$K_L$ is a constant factor, $\vec{Z}(j)$ are the state vectors, $\vec{Z}$ is the state vector, for which the subsequent cycle length should be predicted, $M(\vec{Z})$ is the average over the components of the state vector $\vec{Z}$, $M(\vec{Z}(j))$ is the average over the components of the state vector $\vec{Z}(j)$, $C''(j)=C(j)-M(\vec{Z}(j))$ is the cycle length change calculated from the difference of the subsequent cycle length and the average of the components of the state vector $\vec{Z}(j)$.

Moreover, the above-described improved algorithms provide two decisive advantages:

Firstly, the more precise prediction of the future R waves results in an improved time position of the recorded data and, as a result of this, the realized cardiac phase, at which the images are reconstructed, in turn fits better to the original planning for the scan, which ultimately leads to an increased diagnostic image quality.

Secondly, the improved prediction allows the selection of a smaller interval $C_{min}$, $C_{max}$ for the most probable occurrence of the next R wave, as result of which in turn there is a reduction in the dose applied to the patient. Since prospectively planned modes generally constitute the suitable means for reducing the dose, the dose load on the patient can be reduced decisively.

In the following text, a few concrete examples are shown for predicting the heart rate. In the process, the profile of the measured heart rate as a function of the cycle length in milliseconds is respectively specified by M in the individual illustrations. The curve V shows the profile of the predicted cycle lengths. The region B respectively specifies the most probable interval of the predicted cycle ($C_{min}$, $C_{max}$). Hence, the size of the region B is directly linked to the applied dose.

Figure 6:
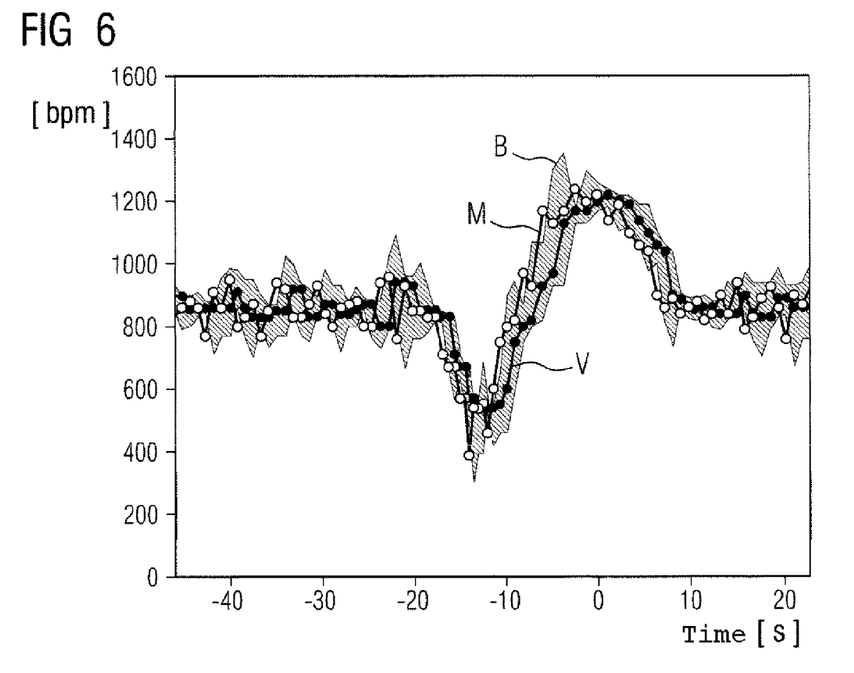
FIG. 6 shows a comparison of a prediction of the length of a future cardiac cycle on the basis of forming the median and the actual values in the case of long-wavelength variation in the heart rate.
Figure 7:
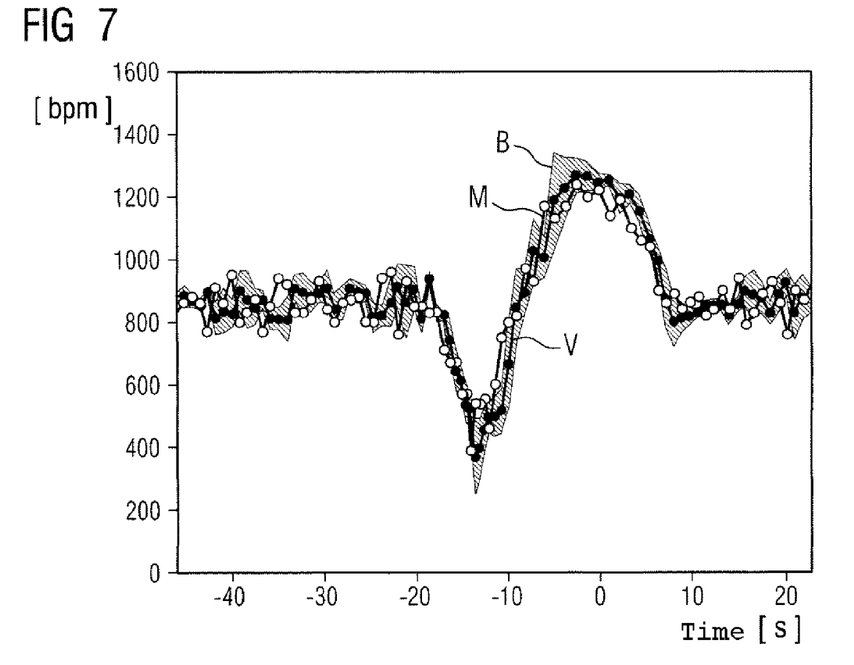
FIG. 7 shows a comparison of a prediction of the length of a future cardiac cycle on the basis of the method according to an embodiment of the invention and the actual values in the case of long-wavelength variation in the cardiac cycle.

FIGS. 6 and 7, 8 and 9, and 10 and 11 show the difference in quality of the predictions. The respective first of two similar figures in each case describes the prediction on the basis of the established method based on the median. The respective second figure of the aforementioned figure pairs shows the prediction as per the above-described algorithm. The abscissa plots the time axis over the measurements and the ordinate plots the cycle duration of the heart in milliseconds. The first figure pair in FIGS. 6 and 7 shows the behavior in an exemplary form for an EKG with long-wavelength variation of the heart rate. This type of variation is typical for a patient asked to hold their breath. This corresponds to the normal workflow in CT. FIG. 6 shows that this long-wavelength variation leads to a phase offset between prediction and reality. The result of this phase offset is that established methods can only look back on a few cycles (median of length 3) without introducing too great an error. By contrast, the proposed method, in this case using a calculation as per the prescription according to one of claims 8 and 9 or as per FIG. 5, only shows slight undershoots and overshoots in FIG. 7 but no phase offset, even though in total the last nine past intervals are included in the prediction.

Figure 8:
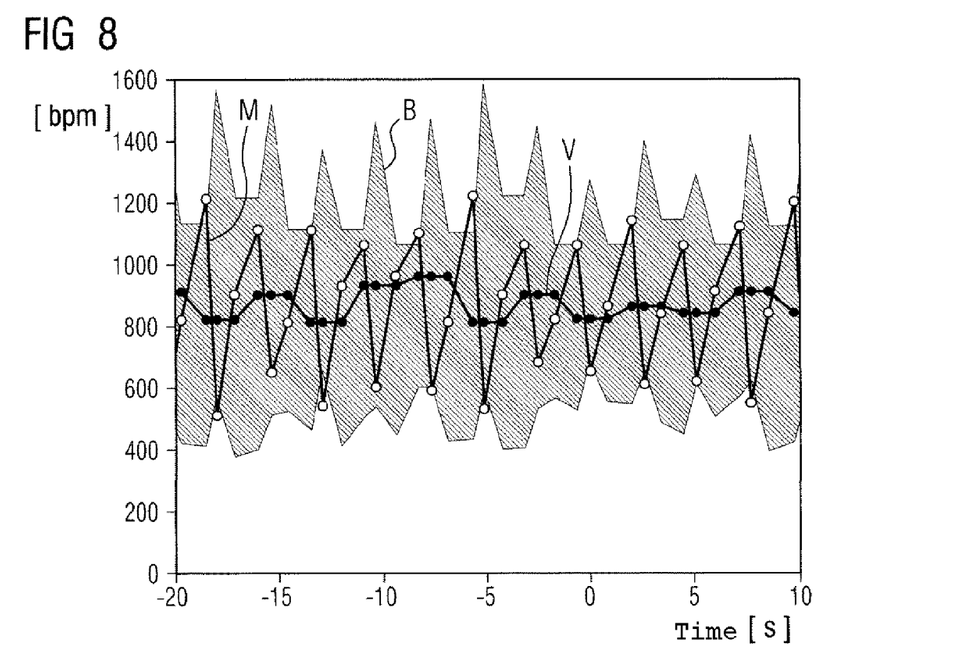
FIG. 8 shows a comparison of a prediction of the length of a future cardiac cycle on the basis of forming the median and the actual values in the case of a heart rate with high variance.
Figure 9:
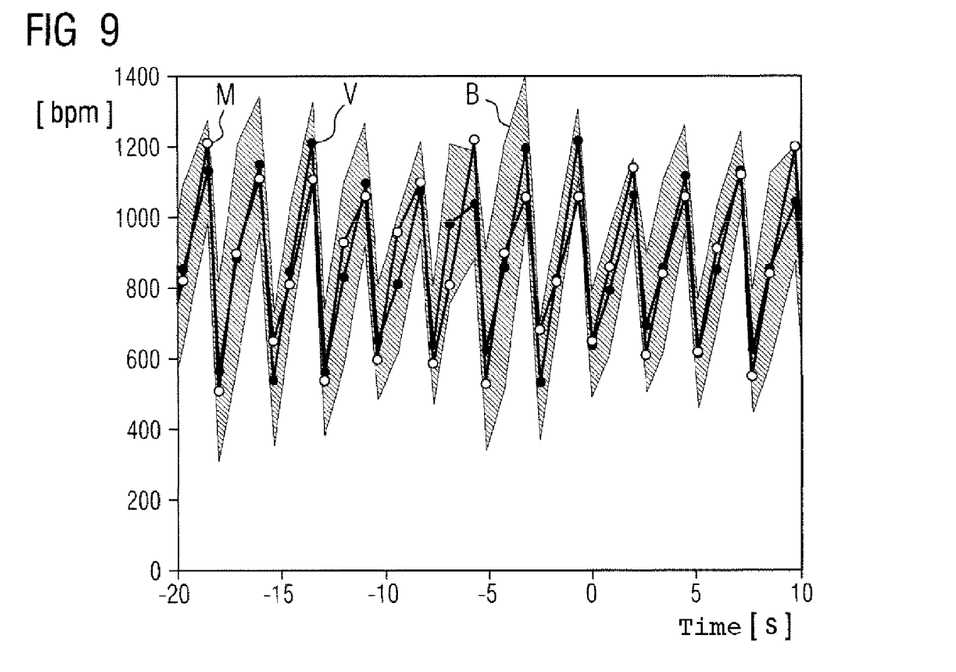
FIG. 9 shows a comparison of a prediction of the length of a future cardiac cycle on the basis of the method according to an embodiment of the invention and the actual values in the case of a heart rate with high variance.

The figure pair in FIGS. 8 and 9 shows an example of a rhythmic pattern that, in the case of a classical prediction in accordance with FIG. 8, leads to a suitable average for the estimate, but leads to much widening of the estimation interval as a result of the large variance, which results in a high patient dose in the case of dose modulation on the basis of this data. The new method, illustrated in FIG. 9, identifies the pattern with high reliability and accuracy, and correspondingly leads to a lower radiation load on the patient.

Figure 10:
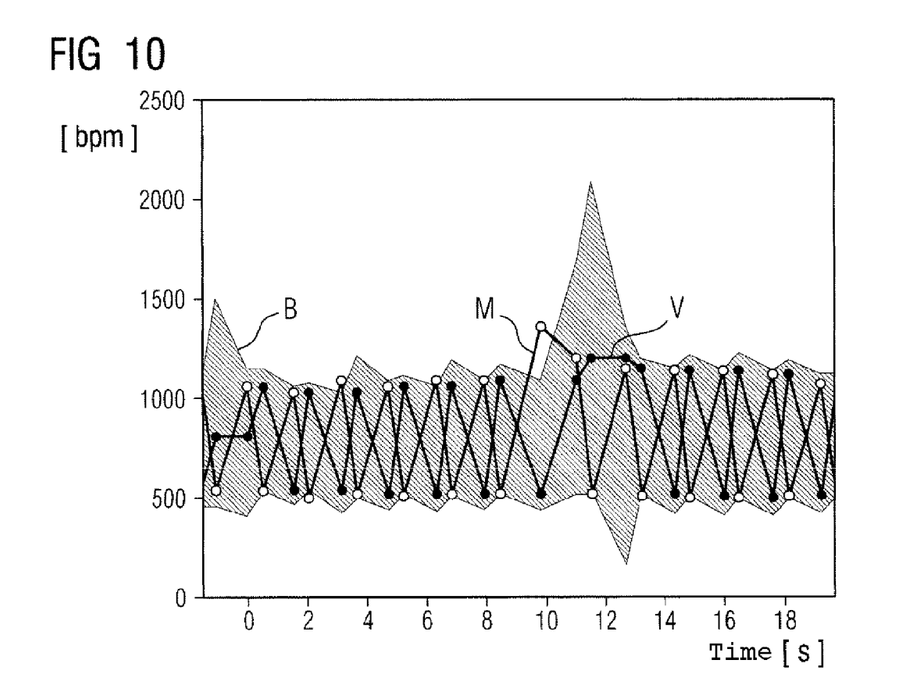
FIG. 10 shows a comparison of a prediction of the length of a future cardiac cycle on the basis of forming the median and the actual values on the basis of the EKG from FIG. 2.
Figure 11:
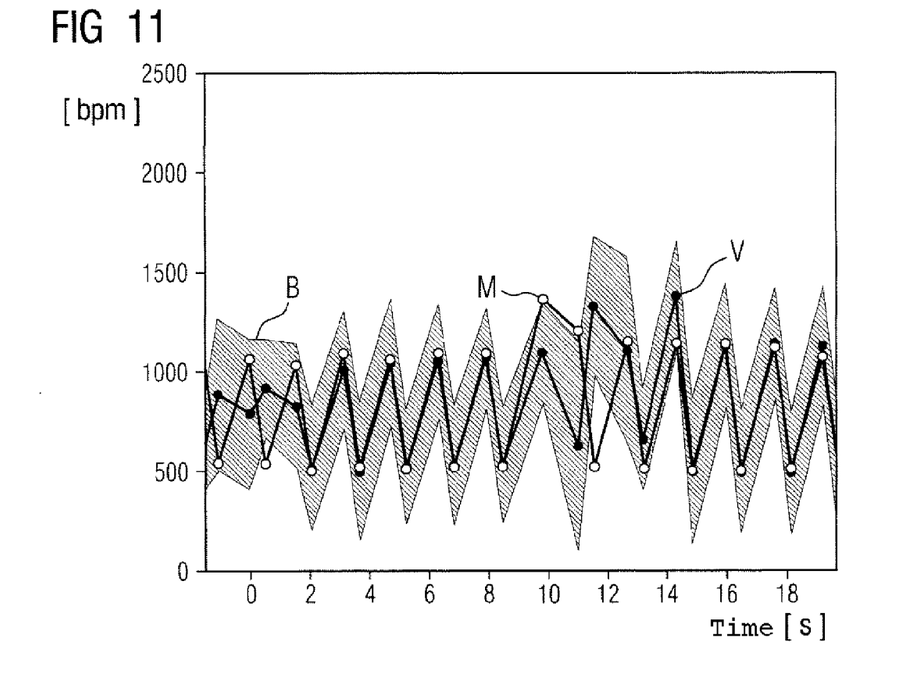
FIG. 11 shows a comparison of a prediction of the length of a future cardiac cycle on the basis of the method according to an embodiment of the invention and the actual values on the basis of the EKG from FIG. 2.

Finally, the last example in the figure pair with FIGS. 10 and 11 shows the prediction for the EKG illustrated in FIG. 2 as a screenshot. FIG. 10 shows that the currently known method fails drastically as a result of the median of length 3 leading the prediction V to run precisely counter to the actual measurements M and additionally generates a very broad region for the most likely interval of the predicted cycle; that is to say this leads to a high dose load on the examined patient. FIG. 11 shows the result of the new algorithm, which identifies the pattern of the present bigeminy very well and can also cope well with the disturbance of the pattern in the center.

It goes without saying that the method described here can also identify patterns of higher order by forming higher-dimensional state vectors. Thus, it is also within the scope of the invention for calculations to be firstly carried out during a learning phase with state vectors with different dimensions and, ultimately, for the calculation to be used in which the dimension is optimally fitted to the present rhythm pattern. In the case of appropriate computing power, it is also possible to carry out parallel predictions on the basis of state vectors with different dimensions and in actual fact to utilize the respectively best-fitting calculation.

It is understood that the aforementioned features of the invention can be used not only in the respective aforementioned combination, but also in other combinations, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for predicting specific cycle phases of a beating heart in a patient within a scope of a CT examination, wherein signal profiles of the heart are continuously recorded during the examination over a multiplicity of cardiac cycles, the method comprising:
determining, by a processor, times of successive cycle positions with the same characteristics, the determining based on the signal profiles and the characteristic signal profiles contained therein;
determining successive cycle lengths of the cardiac cycles based on the determined times;
seeking, progressively concurrently with a present time, patterns in successive cycle lengths over a number of past and successive cardiac cycles;
determining a current or future cycle length by
recording a number of cardiac cycles in the form of state vectors and transferring the vectors into a state space, with each state vector being assigned the value of the subsequent cycle length,
forming a weighted average over the subsequently measured cycle lengths, and
predicting the value of a future cycle based on weightings, the weightings being inversely proportional to the distance between the state vectors recorded for the cycle length and the currently considered state vector for which the prediction is made.

2. The method as claimed in claim 1, wherein a position in time of a certain cycle region is predicted using the predicted cycle length.

3. The method as claimed in claim 2, wherein, within the scope of a CT scan, the dose power of at least one X-ray tube operational for the scan is adjusted using the predicted position in time of the cycle region.

4. The method as claimed in claim 3, wherein image reconstruction takes place within the scope of the CT examination, during which reconstruction only detector data from prescribed cardiac cycle phases is used, or this data is particularly heavily weighted during the image reconstruction, wherein the prescribed cardiac cycle phases of each cycle are determined individually on the basis of the predicted cycle length.

5. The method as claimed in claim 2, wherein
image reconstruction takes place within the scope of the CT examination,
the prescribed cardiac cycle phases of each cycle are determined individually on the basis of the predicted cycle length, and
only detector data from prescribed cardiac cycle phases is used during the image construction, or detector data from prescribed cardiac cycle phases is heavily weighted during the image reconstruction.

6. The method as claimed in claim 1, wherein the cardiac signals used to record the signal profiles are the electrical potentials of the heart.

7. The method as claimed in claim 1, wherein the cardiac signals used to record the signal profiles are pressure changes in or on the arterial circulatory system.

8. The method as claimed in claim 1, wherein, in the process of determining the cycle length to be predicted, a weighting is used that is inversely proportional to the power of the second number.

9. A method for predicting specific cycle phases of a beating heart in a patient within a scope of a CT examination, wherein signal profiles of the heart are continuously recorded during the examination over a multiplicity of cardiac cycles, the method comprising:
measuring, by a processor, cycle lengths within an overall interval with a specific overall number of successive cardiac cycles before the current cycle,
forming subintervals with few successive cycles within this overall interval, and determining a state vector in an L-dimensional space and the associated cycle length of the subsequent cardiac cycle in each subinterval, with L corresponding to the number of successive cycles in each subinterval, and
determining the cycle length of the current cardiac cycle by calculating a weighted average from the associated cycle lengths, wherein the weighting is inversely proportional to the power of the dimension of the L-dimensional space of the state vectors, to the Euclidean distance between the considered state vector with the subsequent cycle length to be predicted and the other state vectors with known subsequent cycle lengths in the L-dimensional space.

10. The method as claimed in claim 9, wherein the cycle length $\hat{C}(\vec{Z})$ to be predicted is calculated by:

$$\hat{C}(\vec{Z}) = \frac{\sum_{j=L+1}^{N} w(j) \cdot C(j)}{\sum_{i=L+1}^{N} w(j)}$$

wherein the following holds true for the weightings w(j):

$$w(j) = \frac{1}{V_0 + K_L |\vec{Z} - \vec{Z}(j)|^L},$$

where
C(j) are the cycle lengths,
i is an index value indicating the index of the cycle for which C(j) is the cycle length,
$V_0$ is a constant factor for preventing the denominator of the expression from equaling 0,
$K_L$ is a constant factor,
$\vec{Z}(j)$ are the state vectors,
$\vec{Z}$ is the state vector, for which the subsequent cycle length should be predicted.

11. A method for predicting specific cycle phases of a beating heart in a patient within a scope of a CT examination, wherein signal profiles of the heart are continuously recorded during the examination over a multiplicity of cardiac cycles, the method comprising:
measuring, by a processor, cycle lengths within an overall interval with a specific overall number of successive cardiac cycles before the current cycle,
forming subintervals with few successive cycles within this overall interval, and determining a state vector in an L-dimensional space and an associated cycle length change in the subsequent cardiac cycle relative to the average of the cycle lengths in the considered subinterval in each subinterval, with L corresponding to the number of successive cycles in each subinterval, determining the cycle length of the current cardiac cycle and the cardiac cycle to be predicted by, calculating a weighted average from the associated cycle length changes, wherein the weighting is inversely proportional to the power of the dimension of the L-dimensional space of the state vectors, to the Euclidean distance between the considered state vector with the subsequent cycle length to be predicted and the other state vectors with known subsequent cycle lengths in the L-dimensional space, and adding the weighted average of the cycle length changes to the average of the cycle lengths in the last subinterval.

12. The method as claimed in the preceding patent claim 11, wherein the cycle length $\hat{C}(\vec{Z})$ to be predicted is calculated by $$\hat{C}(\vec{Z}) = M(\vec{Z}) + \frac{\sum_{j=L+1}^{N} w(j) \cdot C^*(j)}{\sum_{i=L+1}^{N} w(j)}$$

wherein weightings $$w(j) = \frac{1}{V_0 + K_L |\vec{Z} - \vec{Z}(j)|^L},$$

where $K_L$ is a constant factor, $\vec{Z}(j)$ are the state vectors, $C(j)$ are the cycle lengths, j is an index value indicating the index of the cycle for which $C(j)$ is the cycle length, $V_0$ is a constant factor for preventing the denominator of the expression from equaling 0, $\vec{Z}$ is the state vector, for which the subsequent cycle length should be predicted, $M(\vec{Z})$ is the average over the components of the state vector $\vec{Z}$, $M(\vec{Z}(j))$ is the average over the components of the state vector $\vec{Z}(j)$, $C^*(j)=C(j)-M(\vec{Z}(j))$ is the cycle length change calculated from the difference of the subsequent cycle length and the average of the components of the state vector $\vec{Z}(j)$.

13. A CT system for performing a cardiac scan, comprising:

a control and computational unit, including a storage medium for storing at least one computer program, which adapts a dosage power depending on a cardiac cycle during operation in order to reduce the dose load on a patient to be scanned, the program adapting the cardiac-cycle-dependent dose power determines the duration of a current and still ongoing cycle length and/or a cycle region in a still ongoing cardiac cycle by carrying out, when executed on the control and computational unit, the method as claimed in claim 1.

14. A non-transitory computer readable medium including program segments for, when executed on a computer device, causing the computer device to implement the method of claim 1.

* * * * *